United States Patent
Pittman et al.

(10) Patent No.: US 9,743,841 B2
(45) Date of Patent: Aug. 29, 2017

(54) AUTOMATED SLEEP PHENOTYPING

(75) Inventors: Stephen D. Pittman, Brookline, MA (US); Stefanida K. Blake, Jamaica Plain, MA (US); Jacobo D. Reif, Allston, MA (US); David P. White, Boston, MA (US); Erik K. Witt, Murrysville, PA (US)

(73) Assignee: RIC INVESTMENTS, LLC, Wilmington, DE (US)

( * ) Notice: Subject to any disclaimer, the term of this patent is extended or adjusted under 35 U.S.C. 154(b) by 1340 days.

(21) Appl. No.: 12/210,244

(22) Filed: Sep. 15, 2008

(65) Prior Publication Data

US 2009/0082639 A1    Mar. 26, 2009

Related U.S. Application Data

(60) Provisional application No. 60/974,920, filed on Sep. 25, 2007.

(51) Int. Cl.
*A61B 5/0205* (2006.01)
*A61B 5/087* (2006.01)
(Continued)

(52) U.S. Cl.
CPC ............ *A61B 5/0205* (2013.01); *A61B 5/087* (2013.01); *A61B 5/4806* (2013.01); *A61B 5/4812* (2013.01); *A61B 5/4818* (2013.01); *A61B 5/4884* (2013.01); *A61B 5/0488* (2013.01); *A61B 5/0496* (2013.01); *A61B 5/085* (2013.01);
(Continued)

(58) Field of Classification Search
None
See application file for complete search history.

(56) References Cited

U.S. PATENT DOCUMENTS 5,645,053 A * 7/1997 Remmers et al. ....... 128/204.23
6,881,192 B1 * 4/2005 Park .............................. 600/529
(Continued)

FOREIGN PATENT DOCUMENTS

JP    2006516100 A    6/2006
JP    2007512086 A    5/2007
WO   2004032719 A2   4/2004

OTHER PUBLICATIONS

Champagnat et al, "Neural Control of Breathing", Respiratory Research, vol. 2, Suppl 1, 2001, pp. S1-S37.

*Primary Examiner* — Gary Jackson
*Assistant Examiner* — Boniface N Nganga (57) ABSTRACT

A system that determines one or more sleep phenotyping parameters of a subject. In one embodiment, the system comprises a sleep sensor, a stimulus generator, and a processor. The sleep sensor generates signals that convey information related to the physiological functions that indicate the sleep stage of the subject. The stimulus generator provides a stimulus to the subject that enables information related to the sleep phenotyping parameters to be determined. The processor receives the signals generated by the sleep sensor and is in operative communication with the stimulus generator. The processor (i) determines, based on the signals received from the sleep sensor, whether a trigger condition related to the current sleep stage of the subject is satisfied, (ii) controls the stimulus generator to provide the stimulus to the subject if the trigger condition is satisfied, and (iii) quantifies the response of the subject to the stimulus.

9 Claims, 5 Drawing Sheets

(51) Int. Cl.

| | |
|---|---|
| *A61B 5/00* | (2006.01) |
| *A61B 5/0488* | (2006.01) |
| *A61B 5/0496* | (2006.01) |
| *A61B 5/08* | (2006.01) |
| *A61B 5/085* | (2006.01) |
| *A61B 5/11* | (2006.01) |
| *A61B 5/145* | (2006.01) |

(52) U.S. Cl.
CPC ............. *A61B 5/0816* (2013.01); *A61B 5/11* (2013.01); *A61B 5/145* (2013.01)

(56) References Cited

U.S. PATENT DOCUMENTS

| | | | |
|---|---|---|---|
| 6,889,691 B2* | 5/2005 | Eklund et al. | 128/204.21 |
| 6,988,994 B2* | 1/2006 | Rapoport et al. | 600/538 |
| 7,041,049 B1 | 5/2006 | Raniere | |
| 2004/0111041 A1 | 6/2004 | Ni et al. | 600/544 |
| 2004/0138719 A1* | 7/2004 | Cho et al. | 607/42 |
| 2004/0200472 A1* | 10/2004 | Gold | 128/200.24 |
| 2005/0061320 A1* | 3/2005 | Lee et al. | 128/204.18 |
| 2005/0081847 A1* | 4/2005 | Lee et al. | 128/200.24 |
| 2005/0085738 A1* | 4/2005 | Stahmann et al. | 600/529 |
| 2005/0148897 A1* | 7/2005 | Cho et al. | 600/533 |
| 2005/0209511 A1* | 9/2005 | Heruth et al. | 600/301 |
| 2005/0209512 A1* | 9/2005 | Heruth et al. | 600/301 |
| 2005/0209513 A1* | 9/2005 | Heruth et al. | 600/301 |
| 2005/0215847 A1* | 9/2005 | Heruth et al. | 600/26 |
| 2005/0222503 A1* | 10/2005 | Dunlop et al. | 600/323 |
| 2005/0234518 A1* | 10/2005 | Heruth et al. | 607/6 |
| 2006/0009708 A1* | 1/2006 | Rapoport et al. | 600/538 |
| 2006/0037614 A1* | 2/2006 | Madaus | A61B 5/087 128/204.23 |
| 2006/0106275 A1* | 5/2006 | Raniere | 600/26 |
| 2006/0241708 A1* | 10/2006 | Boute | 607/17 |
| 2006/0293608 A1* | 12/2006 | Rothman et al. | 600/545 |
| 2007/0015976 A1* | 1/2007 | Miesel et al. | 600/301 |
| 2007/0032733 A1* | 2/2007 | Burton | 600/509 |
| 2007/0055115 A1* | 3/2007 | Kwok et al. | 600/300 |
| 2007/0083079 A1* | 4/2007 | Lee et al. | 600/27 |
| 2007/0123758 A1* | 5/2007 | Miesel et al. | 600/301 |
| 2007/0191697 A1 | 8/2007 | Lynn et al. | |
| 2007/0208269 A1* | 9/2007 | Mumford | A61B 5/0002 600/546 |
| 2007/0249952 A1* | 10/2007 | Rubin et al. | 600/544 |
| 2008/0009685 A1* | 1/2008 | Kim et al. | 600/300 |
| 2008/0033304 A1* | 2/2008 | Dalal et al. | 600/484 |
| 2008/0039730 A1* | 2/2008 | Pu et al. | 600/484 |
| 2008/0066753 A1* | 3/2008 | Martin et al. | 128/204.23 |
| 2008/0071150 A1* | 3/2008 | Miesel et al. | 600/301 |
| 2008/0251078 A1* | 10/2008 | Buckley | A61M 16/0051 128/204.23 |
| 2009/0078258 A1* | 3/2009 | Bowman et al. | 128/204.26 |
| 2010/0076333 A9* | 3/2010 | Burton et al. | 600/544 |
| 2011/0192400 A9* | 8/2011 | Burton et al. | 128/204.23 |

* cited by examiner

AUTOMATED SLEEP PHENOTYPING

CROSS-REFERENCE TO RELATED APPLICATIONS

This application claims priority under 35 U.S.C. §119(e) from provisional U.S. patent application No. 60/974,920, filed Sep. 25, 2007, the contents of which are incorporated herein by reference.

BACKGROUND OF THE INVENTION

1. Field of the Invention

The invention relates to a system and method for determining information related to one or more sleep phenotyping parameters in an enhanced and automated manner.

2. Description of the Related Art

Various methods and techniques are known for determining information related to information that characterizes the anatomical form and/or function of subjects with respect to their sleep. Particularly, such information may be implemented to characterize the respiration of subjects while sleeping. This information may be represented as parameters that represent a sleep phenotype of the subjects. However, conventional methods and techniques for determining such parameters tend to be labor intensive on the part of a caregiver/information recorder, as adjustments to one or more apparatuses used to control the environment of a subject and/or record information related to the parameter(s) to be determined must be coordinated properly to ensure accuracy. Further, methods and techniques typically used often do not enable determination of a parameter until all of the relevant information has been completely gathered. Other drawbacks associated with these techniques and methods are also known.

SUMMARY OF THE INVENTION

One aspect of the invention relates to a system configured to enable determination of one or more sleep phenotyping parameters of a subject. In one embodiment, the system comprises a sleep sensor, a stimulus generator, and a processor. The sleep sensor is configured to generate one or more output signals that convey information related to the one or more physiological functions that indicate the sleep stage of the subject. The stimulus generator is configured to selectively provide a stimulus to the subject, wherein a response of the subject to the stimulus enables information related to the one or more sleep phenotyping parameters to be determined. The processor receives the one or more output signals generated by the sleep sensor and is in operative communication with the stimulus generator. The processor is also configured (i) to determine based on the one or more output signals received from the sleep sensor, whether a trigger condition related to the current sleep stage of the subject is satisfied, and (ii) to control the stimulus generator to provide the stimulus to the subject if the trigger condition is satisfied.

Another aspect of the invention relates to a method of enabling determination of one or more sleep phenotyping parameters of a subject. In one embodiment, the method comprises generating one or more output signals that convey information about one or more physiological functions of the subject, the one or more physiological functions indicating a sleep stage of the subject; determining, based on the generated one or more output signals, whether a trigger condition related to the current sleep stage of the subject has been met; and providing a stimulus to the subject if it is determined that the trigger condition has been met, wherein a response of the subject to the stimulus enables information related to the one or more sleep phenotyping parameters to be determined.

Another aspect of the invention relates to a system configured to enable determination of one or more sleep phenotyping parameters of a subject. In one embodiment, the system comprises means for generating one or more output signals that convey information about one or more physiological functions of the subject, the one or more physiological functions indicating a sleep stage of the subject; means for determining, based on the generated one or more output signals, whether a trigger condition related to the current sleep stage of the subject has been met; and means for providing a stimulus to the subject if it is determined that the trigger condition has been met, wherein a response of the subject to the stimulus enables information related to the one or more sleep phenotyping parameters to be determined.

Another aspect of the invention relates to a system configured to enable determination of one or more sleep phenotyping parameters of a subject. In one embodiment, the system comprises a sleep sensor, a parameter sensor, and a processor. The sleep sensor is configured to generate one or more output signals that convey information related to one or more physiological functions that indicate a sleep stage of the subject. The parameter sensor is configured to generate one or more output signals that convey information related to one or more physiological functions related to one or more sleep phenotyping parameters of the subject. The processor is in operative communication with each of the sleep sensor and the parameter sensor such that the processor receives the output signals generated by the sleep sensor and the parameter sensor. The processor is configured to determine, based on the one or more output signals received from the sleep sensor, whether a trigger condition related to the current sleep stage of the subject is satisfied, and to determine information related to the one or more sleep phenotyping parameters of the subject based on the one or more output signals generated by the parameter sensor if the trigger condition is satisfied.

Another aspect of the invention relates to a method of enabling determination of one or more sleep phenotyping parameters of a subject. In one embodiment, the method comprises generating one or more output signals related to a sleep stage of the subject, the one or more output signals related to the sleep stage of the subject conveying information related to one or more physiological functions of the subject that indicate a sleep stage of the subject; generating one or more output signals related to one or more sleep phenotyping parameters of the subject, the one or more output signals related to the one or more sleep phenotyping parameters of the subject conveying information related to one or more physiological functions of the subject associated with the one or more sleep phenotyping parameters of the subject; determining, based on the one or more output signals related to the sleep stage of the subject, whether a trigger condition related to the current sleep stage of the subject is satisfied; and determining information related to the one or more sleep phenotyping parameters of the subject based on the one or more output signals related to the one or more sleep phenotyping parameters of the subject generated if the trigger condition is satisfied.

Another aspect of the invention relates to a system configured to enable determination of one or more sleep phenotyping parameters of a subject. In one embodiment, the system comprises means for generating one or more output signals related to a sleep stage of the subject, the one or more output signals related to the sleep stage of the subject conveying information related to one or more physiological functions of the subject that indicate a sleep stage of the subject; means for generating one or more output signals related to one or more sleep phenotyping parameters of the subject, the one or more output signals related to the one or more sleep phenotyping parameters of the subject conveying information related to one or more physiological functions of the subject associated with the one or more sleep phenotyping parameters of the subject; means for determining, based on the one or more output signals related to the sleep stage of the subject, whether a trigger condition related to the current sleep stage of the subject is satisfied; and means for determining information related to the one or more sleep phenotyping parameters of the subject based on the one or more output signals related to the one or more sleep phenotyping parameters of the subject generated if the trigger condition is satisfied.

Another aspect of the invention relates to a system configured to determine information related to sleep phenotyping parameters of a subject. In one embodiment, the system comprises a sleep sensor, a parameter sensor, and a processor. The sleep sensor is configured to generate one or more output signals that convey information related to one or more physiological functions that indicate a sleep stage of the subject. The parameter sensor is configured to generate one or more output signals that convey information related to one or more physiological functions related to two or more sleep phenotyping parameters of the subject. The processor is in operative communication with each of the sleep sensor and the parameter sensor such that the processor receives the output signals generated by the sleep sensor and the parameter sensor. The processor is configured to determine, based on the one or more output signals received from the sleep sensor, whether one or more trigger conditions related to the current sleep stage of the subject are satisfied, wherein individual ones of the one or more trigger conditions correspond to one or more of the two or more sleep phenotyping parameters, and to determine information related to the two or more sleep phenotyping parameters of the subject, wherein the processor is configured to determine information related to a given one of the two or more sleep phenotyping parameters based on the one or more output signals generated by the parameter sensor if the trigger condition that corresponds to the given sleep phenotyping parameter is satisfied, and wherein the two or more sleep phenotyping parameters comprises one or more of a critical pharyngeal closing pressure, upper airway vibration, upper airway muscle responsiveness, arousal threshold, or loop gain.

Another aspect of the invention relates to a method of determining information related to sleep phenotyping parameters of a subject. In one embodiment, the method comprises generating one or more output signals related to a sleep stage of the subject, the one or more output signals related to the sleep stage of the subject conveying information related to one or more physiological functions of the subject that indicate a sleep stage of the subject; generating one or more output signals related to sleep phenotyping parameters of the subject, the one or more output signals related to the sleep phenotyping parameters of the subject conveying information related to one or more physiological functions of the subject associated with the sleep phenotyping parameters of the subject; determining, based on the one or more output signals related to the sleep stage of the subject, whether a first trigger condition related to the current sleep stage of the subject is satisfied; determining information related to a first sleep phenotyping parameter of the subject based on the one or more output signals related to the sleep phenotyping parameters of the subject generated while the first trigger condition is satisfied; determining, based on the one or more output signals related to the sleep stage of the subject, whether a second trigger condition related to the current sleep stage of the subject is satisfied; and determining information related to a second sleep phenotyping parameter of the subject based on the one or more output signals related to the sleep phenotyping parameters of the subject generated while the second trigger condition is satisfied.

Another aspect of the invention relates to a system configured to determine information related to sleep phenotyping parameters of a subject. In one embodiment, the system comprises means for generating one or more output signals related to a sleep stage of the subject, the one or more output signals related to the sleep stage of the subject conveying information related to one or more physiological functions of the subject that indicate a sleep stage of the subject; means for generating one or more output signals related to sleep phenotyping parameters of the subject, the one or more output signals related to the sleep phenotyping parameters of the subject conveying information related to one or more physiological functions of the subject associated with the sleep phenotyping parameters of the subject; means for determining, based on the one or more output signals related to the sleep stage of the subject, whether a first trigger condition related to the current sleep stage of the subject is satisfied; means for determining information related to a first sleep phenotyping parameter of the subject based on the one or more output signals related to the sleep phenotyping parameters of the subject generated while the first trigger condition is satisfied; means for determining, based on the one or more output signals related to the sleep stage of the subject, whether a second trigger condition related to the current sleep stage of the subject is satisfied; and means for determining information related to a second sleep phenotyping parameter of the subject based on the one or more output signals related to the sleep phenotyping parameters of the subject generated while the second trigger condition is satisfied.

Another aspect of the invention relates to a method of diagnosing and treating a sleep-related breathing disorder of a subject. In one embodiment, the method comprises generating one or more output signals related to sleep phenotyping parameters of the subject, the one or more output signals related to the sleep phenotyping parameters of the subject conveying information related to one or more physiological functions of the subject associated with the sleep phenotyping parameters of the subject; determining information related to a plurality of sleep phenotyping parameters, wherein at least one of the plurality of sleep phenotyping parameters is determined based on the one or more output signals related to the sleep phenotyping parameters of the subject; and determining a metric that represents a sleep phenotype of the subject, the metric being derived from the determined information related to the plurality of sleep phenotyping parameters, wherein the sleep phenotype of the subject is indicative of one or more sleep related breathing disorders from which the subject suffers.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
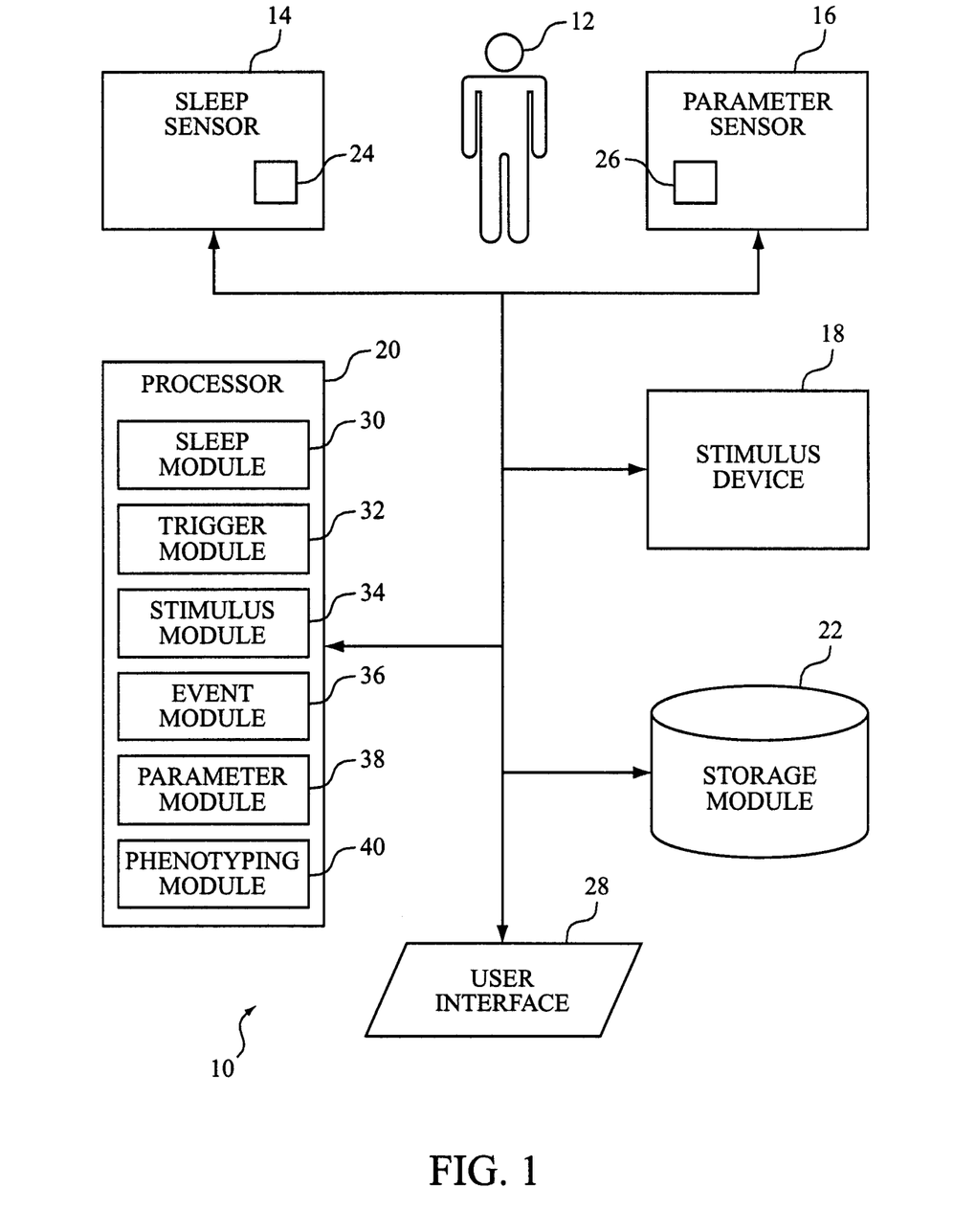
FIG. 1 illustrates a system configured to determine information related to sleep phenotyping parameters of a subject, in accordance with one embodiment of the invention.

FIG. 1 is a schematic diagram of a system 10 configured to determine information related to sleep phenotyping parameters of a subject 12. As used herein, sleep phenotyping parameters comprise metrics that quantify aspects of the physiology and/or physiological performance of the subject 12 that characterize a sleep phenotype of the subject. The sleep phenotype of the subject 12 describes the predisposition of the subject 12 (e.g., due to physiological characteristics of subject 12) to one or more sleep disorders (e.g., obstructive sleep apnea, Cheyne-Stokes breathing, restless legs syndrome, etc.). Examples of sleep phenotyping parameters include critical pharyngeal closing pressure, upper airway vibration characteristics, upper airway muscle responsiveness, arousal threshold, and ventilatory control feedback loop gain. However, it should be appreciated that this list is not intended to be limiting, and in some instances, the system 10 may be configured to determine information related to phenotyping parameters other than those listed here. The present invention also contemplates that a sleep phenotyping parameter can include any combination of the parameters noted above. As can be seen in FIG. 1, in one embodiment, system 10 includes a sleep sensor 14, a parameter sensor 16, a stimulus generator 18, a processor 20, and a storage module 22.

Sleep sensor 14 is configured to monitor one or more physiological functions of subject 12 that indicate a sleep stage of subject 12. More particularly, sleep sensor 14 includes one or more sensor units 24 that generate one or more output signals conveying information related to the one or more physiological functions. For example, sleep sensor 14 may include an electroencephalographic sensor unit, an electromyography sensor unit, an electro-oculographic sensor unit, and/or an oxygen saturation sensor unit. Such sensor units are known in the art to produce data from which the sleep stage of subject 12 may be determined.

Further, sleep sensor 14 may include other, less traditional, sensor units, such as a respiratory sensor unit, an actimetry sensor unit, an arterial tonometry sensor unit, and/or other sensor units that generate output signals that convey information related to one or more physiological functions that vary in a predictable manner with the sleep stage of subject 12.

A respiratory sensor unit would include a sensor unit that generates output signals that convey information about the respiration of the subject 12 (e.g., breath rate, respiration volume, constituent concentration levels, respiration flow, pressure at or near the upper airway of subject 12, etc.). Such sensor units include a pressure sensor unit, a flow sensor unit, and/or other sensor units. An actimetry sensor unit would include a sensor unit that generates output signals that convey information related to the position and/or movement of subject 12. For instance, an actimetry sensor unit may include a position sensor unit, a vibration sensor unit, a sound sensor unit, an accelerometer sensor unit, and/or other sensor units.

Parameter sensor 16 is configured to monitor one or more physiological functions of subject 12 related to the one or more sleep phenotyping parameters of subject 12. To monitor the one or more physical functions of subject 12 related to the one or more sleep phenotyping parameters of subject 12, parameter sensor 16 includes one or more sensor units 26 that generate output signals conveying information related to the one or more physiological functions. For example, parameter sensor 16 may include a respiratory sensor unit (e.g., monitoring function(s) related to airflow, monitoring function(s) related to respiratory effort, etc.), a cardiovascular sensor unit, a vibration sensor unit, an actimetry sensor unit, an electromyography sensor unit, an oxygen saturation sensor unit, a carbon dioxide sensor unit, an electroencephalographic sensor unit, an electro-oculographic sensor unit, and/or other sensor units that monitor one or more physiological functions that are related to a sleep phenotyping parameter of subject 12.

Stimulus generator 18 is configured to selectively provide a stimulus to subject 12. The stimulus provided to subject 12 is such that a response of subject 12 to the stimulus enables the gathering of information related to one or more sleep phenotyping parameters. For example, as will be discussed further below, a stimulus is provided by stimulus generator 18 to subject 12 in order to determine information related to the critical pharyngeal closing pressure, upper airway muscle responsiveness, arousal threshold, and loop gain. In some instances, stimulus generator 18 is configured to provide aid to subject 12, and the provision of the stimulus to subject 12 includes halting, reducing, and/or altering the aid being provided to subject 12. As an example of this, in one embodiment, stimulus generator 18 comprises a device that provides a flow of pressurized gas to the airway of subject 12 to support the airway during sleep (e.g., a Positive Airway Pressure device ("PAP device")). Provision of the stimulus to subject 12 by such a stimulus generator 18, in some cases (e.g., those described below), includes reducing the pressure of the flow of gas to levels at which subject 12 is susceptible to respiratory challenges (e.g., apneas, airway obstructions, etc.). Although stimulus generator 18 is referred to in the application in the singular, as used herein the term "stimulus generator" should be construed to include a single device providing a single stimulus, a single device capable of selectively providing a plurality of different stimuli to subject 12, a plurality of devices that selectively provide a single stimulus to subject 12, and/or a plurality of devices configured to selectively provide a plurality of different stimuli to subject 12.

It should be appreciated from the description of sleep sensor 14, parameter sensor 16, and stimulus generator 18 above, that although these components are illustrated in FIG. 1 as single, discrete components, this is for illustrative purposes only. For example, in one embodiment, sleep sensor 14 and parameter sensor 16 include one or more common sensor units, as the physiological functions relevant to determining a sleep stage of subject 12 may also be relevant to determining information related to one or more sleep phenotyping parameters. In one embodiment, stimulus generator 18 includes one or more sensor units that monitor the provision of the stimulus to subject 12 (e.g., a flow sensor unit and/or a pressure sensor unit included in a PAP device), and at least one of the one or more sensor units that monitor the provision of the stimulus to subject 12 also functions as a sensor unit 24 and/or 26 in one or both of sleep sensor 14 and parameter sensor 16. The co-implementation of components (e.g., sensor units) within sleep sensor 14, parameter 16, and/or stimulus generator 18 may include a physical integration of all or part of sensors 14 and 16 and/or stimulus generator 18. In other configurations, sensors 14 and 16 and stimulus generator 18 are maintained discretely from each other.

Storage module 22 provides electronic storage capabilities for system 10. Storage module 22 includes one or more electronically readable storage media that are operatively coupled with one or more of sleep sensor 14, parameter sensor 16, stimulus generator 18, and/or processor 20. This operative couple is illustrated in FIG. 1. The electronically readable storage media of storage module 22 may include one or both of system storage that is provided integrally (i.e., substantially non-removable) with system 10 and removable storage that is removably connectable to system 10 via, for example, a port (e.g., a USB port, a firewire port, etc.) or a drive (e.g., a disk drive, etc.). Storage module 22 may include optically readable storage media (e.g., optical disks, etc.), magnetically readable storage media (e.g., magnetic tape, magnetic hard drive floppy drive, etc.), solid-state storage media (e.g., flash drive, etc.), and/or other electronically readable storage media. In one embodiment, storage module 22 may include a smart card with writeable memory that receives information from and provides information to system 10 wirelessly. Storage module 22 may store software algorithms, information related to the output signals generated by one or both of sensors 14 and 16, information determined by processor 20, and/or other information that enables processor 20 to function properly. Storage module 22 may be a separate component within system 10, or storage module 22 may be provided integrally with one or more of sensors 14 and 16, stimulus generator 18, or processor 20.

In one embodiment, system 10 further includes a user interface 28. User interface 28 provides an interface between system 10 and one or more users (e.g., a caregiver, a researcher, subject 12, etc.) through which users may provide information to and receive information from system 10. This enables data, results, and/or instructions and any other communicable items, collectively referred to as "information", to be communicated between the user(s) and one or more of sleep sensors 14, parameters sensors 16, stimulus generator 18, processor 20 and/or storage module 22. This information may be communicated from user interface 28 to system 10 by an operative communication link illustrated in FIG. 1 by an arrow. Examples of conventional interface devices suitable for inclusion in user interface 28 include a keypad, buttons, switches, a keyboard, knobs, levers, a display screen, a touch screen, speakers, a microphone, an indicator light, and a printer. User interface 28 may be a separate component within system 10, or user interface 28 may be provided integrally with one or more of sensors 14 and 16, stimulus generator 18, processor 20, or storage module 22.

It is to be understood that other communication techniques, either hard-wired or wireless, are also contemplated by the present invention as user interface 28. For example, the present invention contemplates that user interface 28 may be integrated with a removable storage interface provided by storage module 22. In this example, information may be loaded into system 10 from removable storage (e.g., a smart card, a flash drive, a removable disk, etc.) that enables the user(s) to customize the implementation of system 10. Other exemplary input devices and techniques adapted for use with the pressure support system 10 as user interface 28 include, but are not limited to, an RS-232 port, RF link, an IR link, modem (telephone, cable or other). In short, any technique for providing information to system 10 is contemplated by the present invention as user interface 28.

Processor 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may include a plurality of processing units. These processing units may be physically located within the same device, or processor 20 may represent processing functionality of a plurality of devices operating in coordination. In instances in which a plurality of devices are implemented, operative communications links may be formed between the devices to enable communication and coordination therebetween. For example, in some embodiments, processor 20 may include one or more processors external to the other components of system 10 (e.g., a host computer), one or more processors that are included integrally in one or more of the components of system 10 (e.g., one or more processors included integrally with one or more of sensors 14 and 16, stimulus generator 18, storage module 22, etc.), or both. Processors external to other components within system 10 may, in some cases, provide redundant processing to the processors that are integrated with components in system 10, and/or the external processor(s) may provide additional processing to determine additional information related to the operation of system 10 and/or the determination of sleep phenotyping parameters of subject 12.

As is shown in FIG. 1, in one embodiment, processor 20 includes a sleep module 30, a trigger module 32, a stimulus module 34, an event module 36, a parameter module 38, and a phenotype module 40. Modules 30, 32, 34, 36, 38, and 40 may be implemented in software; hardware; firmware; some combination of software, hardware, and/or firmware; and/or otherwise implemented. It should be appreciated that although modules 30, 32, 34, 36, 38, and 40 are illustrated in FIG. 1 as being co-located within a single processing unit, in implementations in which processor 20 includes multiple processing units, modules 30, 32, 34, 36, 38, and/or 40 may be located remotely from the other modules and operative communication between modules 30, 32, 34, 36, 38, and/or 40 may be achieved via one or more communication links. Such communication links may be wireless or hard wired.

Sleep module 30 is configured to determine information related to a current sleep stage of subject 12 based on the one or more output signals generated by sleep sensor 14. In one embodiment, determining information related to the current sleep stage includes determining the sleep stage directly from the output signals. In one embodiment, determining information related to the current sleep stage includes first determining a physiological function of subject 12 from the output signals, and then determining information related to the current sleep stage (e.g., determining the sleep stage) based on the determined physiological function. In this embodiment, the determined physiological function may further be implemented in the control of system 10 and/or the analysis of the sleep phenotype of subject 12.

As is discussed further below, in determining information related to sleep phenotyping parameters of subject 12, the subject is observed (e.g., by sensor units 26 of parameter sensor 16) while he/she is sleeping. In the case of some sleep phenotyping parameters, relevant information is determined from observation of subject 12 in predetermined stages of sleep and/or during transitions between predetermined stages of sleep. Accordingly, trigger module 32 is configured to determine, based on the one or more output signals generated by sleep sensor 14, whether a trigger condition related to the current sleep stage of subject 12 is satisfied. In one embodiment, determining whether a trigger condition is satisfied includes comparing the information determined by sleep module 30 with the trigger condition. Trigger conditions are set such that they are satisfied when subject's 12 sleep stage is such that observation of one or more of her physiological functions will enable determination of at least one phenotyping parameter, or related information.

For example, in one embodiment, a given trigger condition comprises a requisite sleep stage such that the given trigger condition is satisfied if the current sleep stage of subject 12 (e.g., as determined by sleep module 30) is the requisite sleep stage.

In one embodiment, the given trigger condition farther requires that the current sleep stage of subject 12 remain at the requisite sleep stage for a predetermined amount of time before the trigger condition is satisfied.

As another example, in one embodiment, a given trigger condition comprises a threshold measurement of at least one of the physiological functions monitored by sleep sensor 14 such that if the physiological function(s) crosses the threshold measurement, the trigger condition is satisfied. With this type of trigger condition, trigger module 32 may implement information related to the physiological function(s) determined by sleep module 30 (as discussed above), or trigger module 32 may simply compare the output signals generated by sleep module 30 with a signal threshold. Similar to the previous example, in some instances, the given trigger condition may further require that the physiological function(s) remain across the threshold measurement for a predetermined amount of time before the trigger condition is satisfied.

Stimulus module 34 is configured to control stimulus generator 18 to selectively provide stimulation to subject 12 such that a response of the subject to the stimulation will enable the determination of information related to one or more sleep phenotyping parameters. The control of stimulus module 34 over stimulus generator 18 is based on the satisfaction of one or more trigger conditions. In one exemplary embodiment, information related to a given sleep phenotyping parameter may be determined from a response of subject 12 to a corresponding response when subject 12 is experiencing stable Non-Rapid Eye Movement sleep ("NREM" sleep) (selected merely for illustrative purposes). Accordingly, stimulus module 34 is configured such that if trigger module 32 determines that the current sleep stage of subject 12 satisfies a trigger condition associated with stable NREM sleep, stimulus generator 18 is controlled to initiate provision of the stimulation to subject 12. In some instances, the provision of the stimulation to subject 12 is continued according to a predetermined algorithm regardless of the reaction of subject 12 to the stimulation. In other instances, the provision of the stimulation may be altered based on the response of subject 12 (e.g., as discussed below with respect to event module 36), or the stimulation may be halted or paused altogether (e.g., based on a determination by trigger module 32 that the trigger condition associated with stable NREM sleep is no longer satisfied). Further description of examples of the control of stimulus module 34 over stimulus generator 18 to enable determination of some non-limiting specific examples of sleep phenotyping parameters are provided below.

In order to determine information related to some phenotyping parameters, subject 12 must be observed before, during, or after a certain type of physiological event. This may include observation of the subject prior to the event, at the beginning of the event, while the event is ongoing, at the end of the event, and/or subsequent to the event. By way of non-limiting example, the event may include a respiratory event (e.g., an inhalation, an exhalation, a flow limited breath, an apnea, a hypopnea, upper airway instability, snoring, an airway blockage, etc.). Such examples are discussed further below with respect to specific sleep phenotyping parameters. Event module 26 is configured to identify events based on the output signals generated by parameter sensors 16. This includes the identification of transition into, out of, and/or within the events.

Parameter module 38 is configured to determine information related to one or more sleep phenotyping parameters based on the output signals generated by parameter sensor 16. In one embodiment, the determined information includes information related to the one or more physiological functions of subject 12 monitored by sleep sensor 14 and/or parameter sensor 16. By way of non-limiting example, the one or more sleep phenotyping parameters may include one or more of a critical pharyngeal closing pressure ("critical pressure"), upper airway vibration, upper airway muscle responsiveness, arousal threshold, loop gain, and/or other sleep phenotyping parameters. As should be appreciated from the discussion of some sleep phenotyping parameters that may be determined by parameter module 38 that follows, in one embodiment, parameter module 38 determines this information in real-time or near real-time. However, this is not intended to be limiting, as parameter module 38 may determine one or more of the sleep phenotyping parameters based on previously stored information. Further, in one embodiment, a given parameter is determined in real-time or near real-time, and then is refined at some later time based on additional information.

In one embodiment, parameter module 38 is configured to determine information related to the critical pressure of subject 12. The critical pressure is the pressure at which the upper airway of subject 12 collapses and an obstructive apnea develops. This includes providing a pressurized flow of breathable gas to the upper airway of subject 12 (e.g., via stimulus generator 18 as described above) to support the airway until subject 12 enters an appropriate stage of sleep (e.g., stage 2 sleep). The determination that subject 12 has entered the appropriate stage of sleep is made by sleep module 30 and/or trigger module 32 (e.g., as a trigger condition). Once subject 12 has entered the appropriate stage of sleep a respiratory stimulus, or "challenge," is provided to subject 12 by stimulus generator 18 (as controlled by stimulus module 34). The stimulus includes reducing the pressure of the airway to a first reduced pressure. The response of subject 12 to the stimulus is then monitored by parameter sensor 16 (e.g., the response is reflected in the output signals generated by parameter sensor 16). For example, information related to the flow of inhalation(s) and/or exhalation(s) of subject 12 while the stimulus is being provided is reflected in the output signals generated by parameter sensor 16. The information related to the flow of inhalation(s) and/or exhalation(s) of subject 12 may include flow rate, volume, and/or other information related to the flow of gas through the airway of subject 12. The stimulus is then terminated (e.g., the pressure of the airway is returned to the pressure prior to the provision of the stimulus). This process is repeated at a plurality of different levels of stimuli (e.g., different reduced pressures are applied as stimuli), and based on the response of subject 12 to the stimuli, the critical pressure is determined.

If trigger module 32 determines at any point during this process that the stability of subject 12 has fallen below a predetermined threshold (e.g., comes out of the appropriate sleep stage, etc.) a trigger condition may be satisfied that ceases or pauses the provision of stimuli to subject 12. If such a trigger condition is satisfied, trigger module 32 again monitors the sleep of subject 12 until a trigger condition is satisfied that indicates that the sleep of subject 12 is stable enough to permit the provision of stimuli to be resumed.

Figure 2:
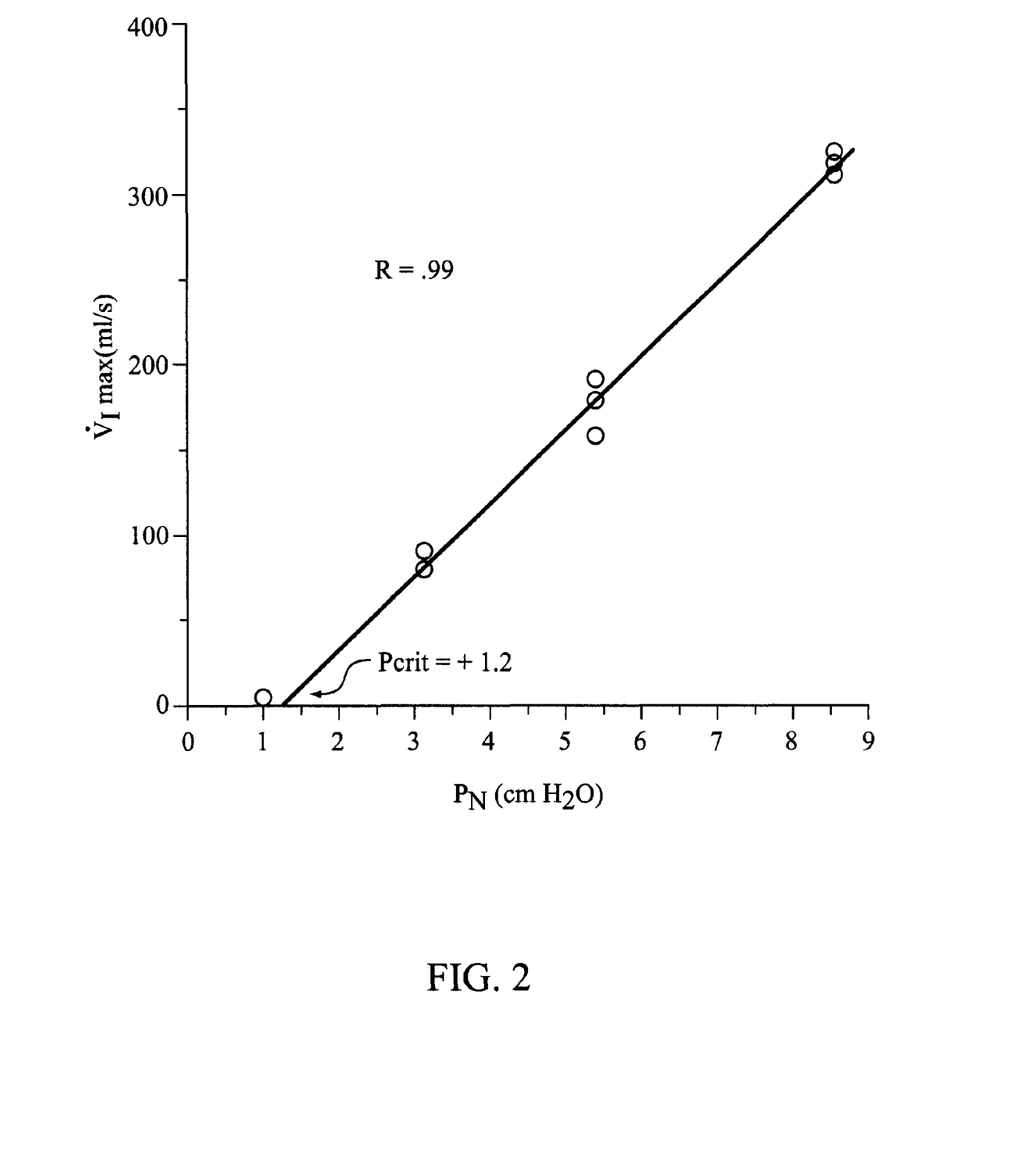
FIG. 2 illustrates a plot used to determine a critical pharyngeal closing pressure of a patient, in accordance with one embodiment of the invention.

As has been indicated above, in one embodiment, the stimulus includes reducing the pressure of the airway of subject 12. In this embodiment, the critical pressure is determined by plotting the information related to the flow of subject 12's breathing against the reduced pressure provided to subject 12 as a stimulus, and then determining (e.g., via a linear regression) the pressure at which the flow of subject 12's breathing goes to zero. For example, FIG. 2 illustrates such a plot.

Figure 3:
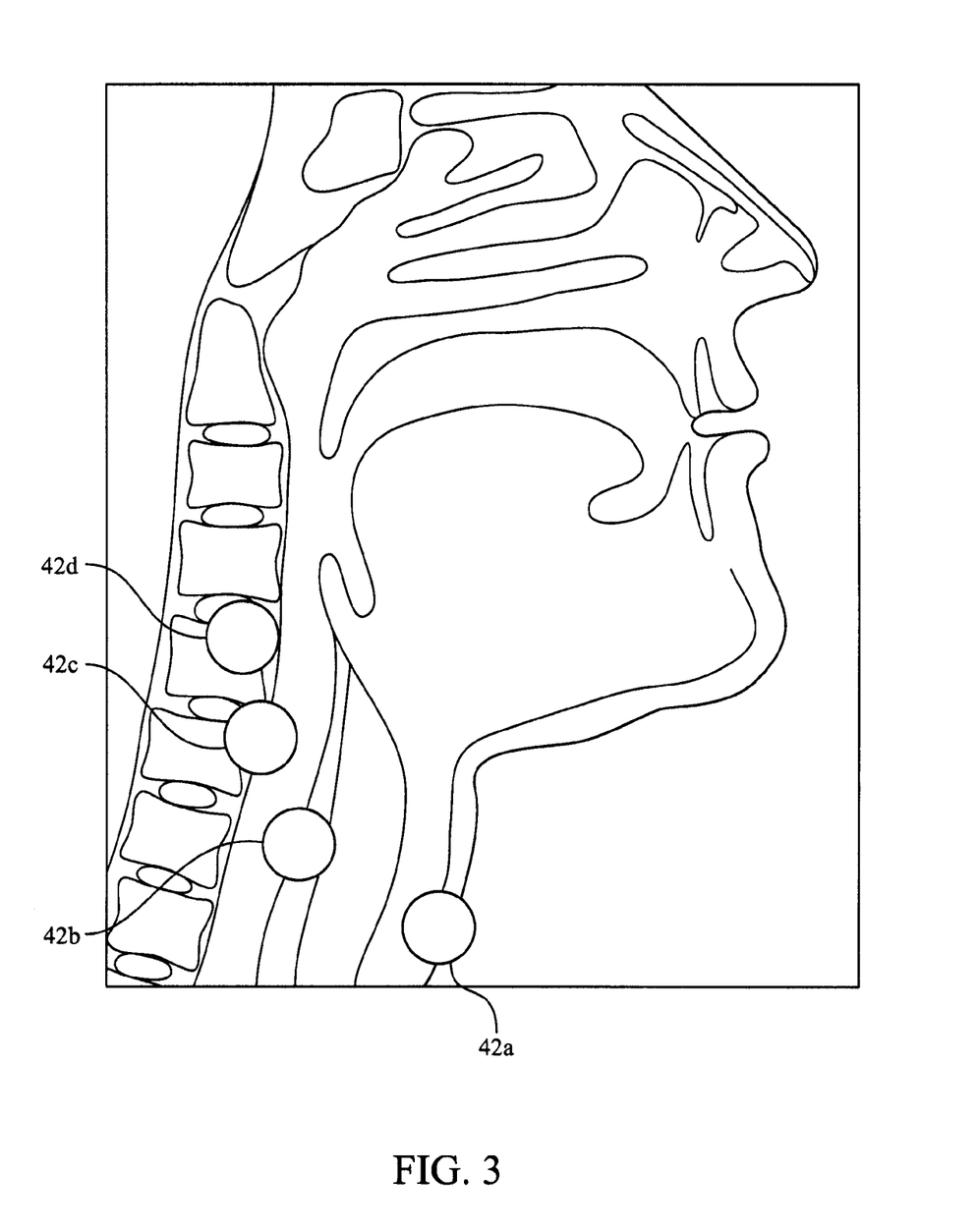
FIG. 3 illustrates the placement of sensor units on a subject, according to one embodiment of the invention.

Returning to FIG. 1, in one embodiment, parameter module 38 determines information related to the vibration of the upper airway of subject 12. In such an embodiment, sensor devices 26 of parameter sensor 16 includes a plurality of vibration sensors on subject 12 to monitor the vibration of the upper airway. For example, FIG. 3 illustrates the placement of 4 sensor devices 42a-42d on the neck of subject 12. Based on the signals generated by sensor devices 42a-42d, information related to the source of airway obstructions may be determined. In order to ensure that information determined based on the output signals of sensor devices 42a-42d reflects the vibration of subject 12's neck during sleep, the output signals generated by sensor devices 42a-42d may be discarded if a trigger condition related to some predetermined level of stable sleep is not determined by trigger module 32 to be satisfied. Alternatively, information determined based on the output signals of sensor devices 42a-42d when the trigger condition is not satisfied may be marked or flagged as so that it will not be implemented in determining information related to the airway anatomy of subject 12.

Returning to FIG. 1, in one embodiment, parameter module 38 determines information related to upper airway muscle responsiveness of subject 12. In order to determine such information, stimulation is provided to subject 12 while subject 12 is asleep. As was the case with each of critical pressure and airway vibration, the determination as to whether subject 12 is sleeping with an appropriate stability is made by trigger module 32 and the provision of stimuli to subject 12 is initiated and paused and/or ceased based on this determination. The stimulation is provided by stimulus generator 18 (as controlled by stimulus module 34) and includes reducing the pressure of the upper airway of subject 12 so that subject 12 experiences flow limited breathing. In one embodiment, parameter module 38 then determines information related to upper airway muscle responsiveness based on the number of breaths and/or amount of time that it takes for the breathing of subject 12 to return to normal. This determination is based on output signal(s) of one or more sensor devices 26 of parameter sensor 16 that convey information related to the flow of gas through the upper airway of subject 12. It should be appreciated that this is not intended to be limiting. For example, in one embodiment, parameter sensor 16 includes an intraoral or sublingual EMG electrode, and information related to upper airway responsiveness is determined based on output signals from such an electrode.

In one embodiment, parameter module 38 determines information related to the arousal threshold of subject 12. The arousal threshold corresponds to the maximal respiratory effort developed in response to a respiratory event at which subject 12 becomes aroused. In order to determine information related to this parameter, a stimulus is provided to subject 12 while the subject is asleep. The determination that subject 12 has attained sleep of an appropriate stability may be made by trigger module 32, for example, in the manner discussed above with respect to the determination of critical pressure and/or airway vibration. Once the subject's sleep reaches an appropriate level, a stimulus is provided to subject 12 by stimulus generator 18 to wake the subject. The stimulus may include one or more of decreasing the pressure of the airway of subject 12, increasing the carbon dioxide inhaled by the subject (e.g., by re-breathing), and/or decreasing the oxyhemoglobin saturation of the subject. Such stimulus is provided to subject 12 in an incremental manner until arousal takes place. In one embodiment, parameter sensor 16 includes a sensor unit that monitors the effort expended by subject 12 at arousal directly (e.g., an effort belt worn by the subject that monitors muscle contraction). In another embodiment, information related to the arousal threshold of subject 12 is determined based on the magnitude of the stimulus (e.g., the decrease in pressure at the airway, the increase in carbon dioxide inhalation, the decrease in oxyhemoglobin saturation, etc.) required to wake the subject from stable sleep. The determination as whether subject 12 has been wakened is made by trigger module 32.

In one embodiment, parameter module 38 determines information related to ventilatory control feedback loop gain of subject 12. In the human anatomy, gas exchange between blood and atmosphere occurs in the lungs. However, respiration is controlled based on levels of these gases (e.g., oxygen, carbon dioxide, etc.) present in the blood when it reaches the brain. Therefore, there is a lag between an increase or decrease in the levels of these gases in the blood as it leaves the lungs and the detection of the change at the brain. Respiration increases with an increasing level of carbon dioxide and the rate of this increase in respiration rises with a lack of oxygenation. Further, a response to a lack of oxygenation (e.g., or a surplus of carbon dioxide) in the blood (e.g., taking in more oxygen) is inhibited by flow limited breathing. The loop gain of subject 12 is related to the amount of time it takes for the subject to be able to correct a fluctuation in the oxygenation level (e.g., or the carbon dioxide level) of the blood. This correction time is a function of both circulation (e.g., the amount of time it takes for the blood to reach the brain from the lungs) and breathing effort (e.g., as impacted by the change in respiration for a given stimulus to subject 12 and sleep induced respiratory events such as flow limited breathing).

In one embodiment, in order to determine information related to loop gain of subject 12, stimulus is provided to the subject while the subject is asleep. The stability of the sleep of subject 12 is determined by trigger module 32, as described above, and if the subject wakes up during the provision of the stimulus to the subject, then the provision is paused or ceased until the stability of the sleep of the subject again becomes sufficient. The stimulus is applied by stimulus generator 18 and includes decreasing the level of carbon dioxide in the gas present at the airway of subject 12. This may be accomplished, for example, by increasing the pressure and/or the flow rate of the flow of gas provided to the airway of subject 12, increasing minute ventilation, which will decrease the carbon dioxide inhaled by the subject as a result of washing out carbon dioxide from the airway.

At some point, as the carbon dioxide inhaled by subject 12 decreases, the breathing of the subject will begin to crescendo-decrescendo to regulate the level of oxygen/carbon dioxide in the blood. This crescendo-decrescendo of breathing can be detected based on the output signals generated by parameter sensor 16 (e.g., conveying information related to the flow of gas at the upper airway). Information related to the decrease in carbon dioxide inhaled by subject 12 (e.g., information related to the increase in pressure) that causes the crescendo-decrescendo of breathing can be implemented to characterize the loop gain of subject 12. It should be appreciated that this technique is not intended to be limiting, and that other techniques, such as pseudo random binary sequence, pressure reduction across multiple breaths, and/or proportional assist ventilation, may be implemented by parameter module 38 to characterize ventilatory control feedback loop gain.

In one embodiment, parameter module 38 obtains information related to one or more sleep phenotyping parameters from a user of system 10. The user may include subject 12, a care-provider, a researcher, etc. The user provides the information to parameter module 38 by inputting the information to system via user interface 28. For example, the user may provide information related to patient-reported symptoms or responses to predetermined questions (e.g., the Epworth Sleepiness Scale, the Pittsburgh Sleep Quality Index, etc.).

Phenotyping module 40 is configured to determine a sleep phenotype of subject 12 based on the one or more sleep phenotyping parameters determined by parameter module 38. Determining the phenotype of subject 12 may include determining a metric that represents the sleep phenotype of the subject. The sleep phenotype of subject 12 may be indicative of one or more sleep related breathing disorders from which the subject suffers. In one embodiment, phenotyping module 40 determines the sleep phenotype in real-time or near real-time. As noted above, the sleep phenotyping parameters include, but are not limited to a critical pharyngeal closing pressure, upper airway vibration, upper airway muscle responsiveness, arousal threshold, or loop gain.

Phenotyping module 40 may leverage the determined sleep phenotype to prescribe treatment for subject 12 likely to be successful in treating the one or more sleep related breathing disorders suffered by the subject. In embodiments in which phenotyping module 40 determines the sleep phenotype of subject 12 in real-time or near real-time, system 10 may apply the prescribed treatment instantaneous (or substantially so) with the determination of the sleep phenotype. This may enable the responsiveness of subject 12 to the prescribed treatment to be monitored during the same period of sleep as the testing conducted to determine the one or more sleep phenotyping parameters.

In one embodiment, the information related to sleep phenotyping parameters determined by parameter module 38 includes numeric scores for individual sleep phenotyping parameters. These scores are then implemented by sleep phenotyping module 40 to determine the metric. For example, the scores may be aggregated (e.g., by averaging, by weighted averaging, etc.) to determine a single score that represents the sleep phenotype of patient 12.

Figure 4:
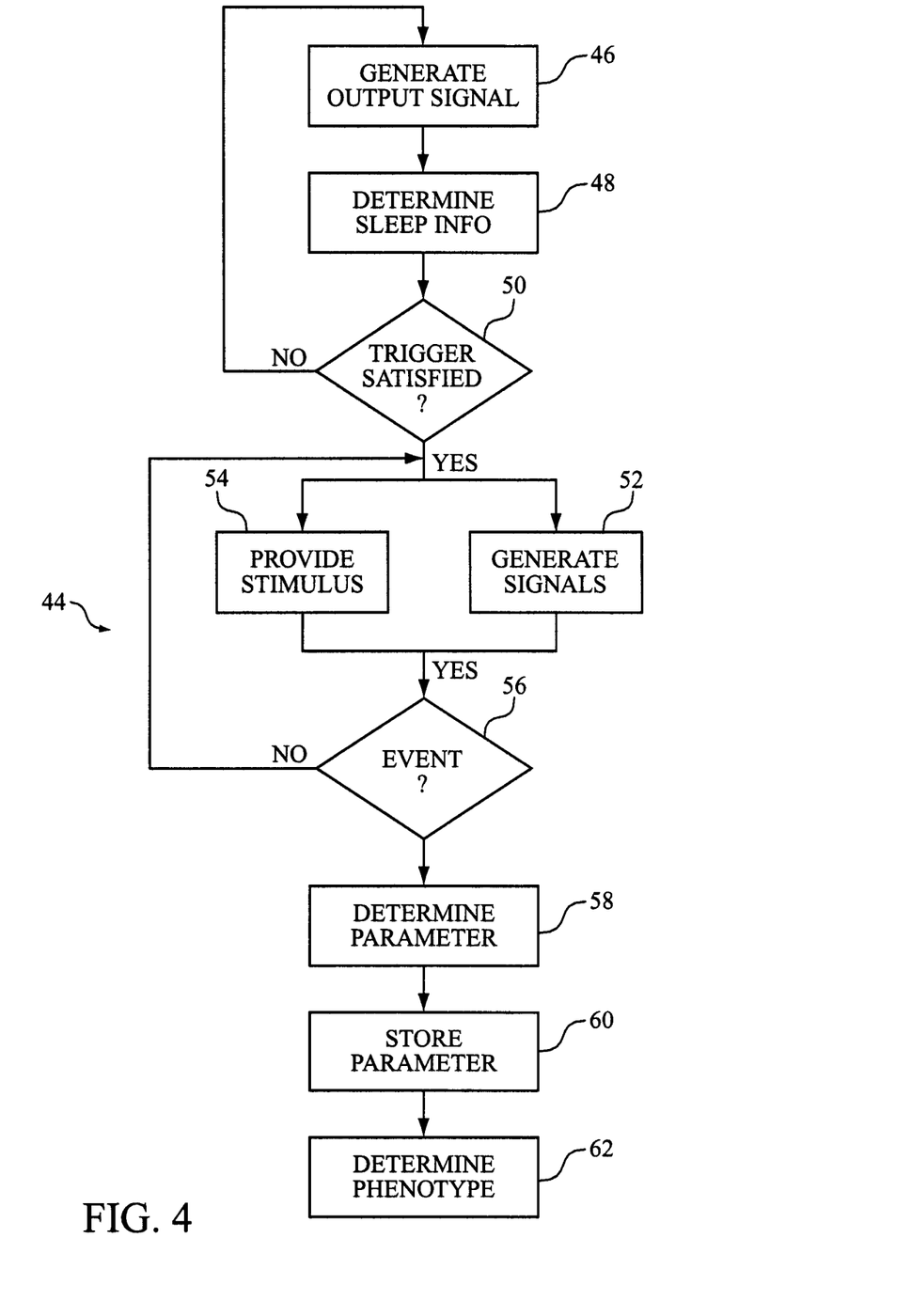
FIG. 4 illustrates a method of determining information related to a phenotyping parameter of a patient, according to one embodiment of the invention.
Figure 5:
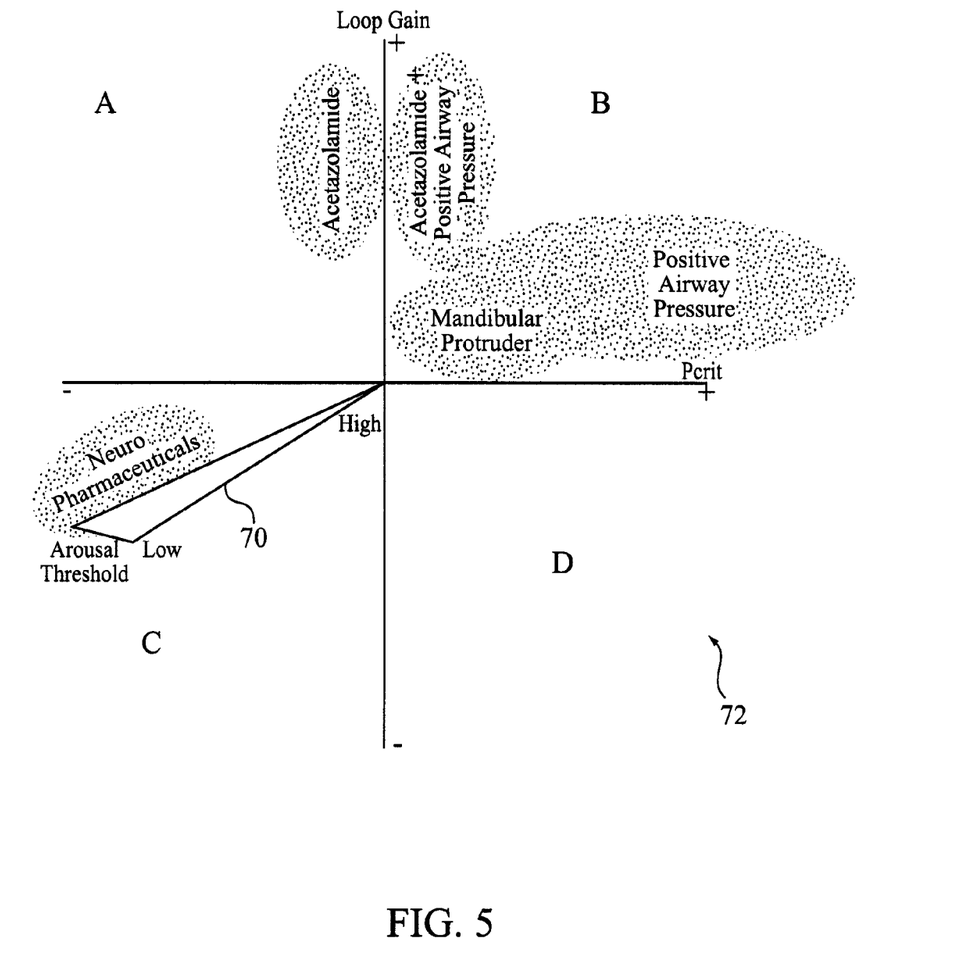
FIG. 5 is a chart illustrating an example of phenotype clusters and potential therapies for 3 parameters in 3 dimensions.

As another example, the scores determined by parameter module 38 are used to determine a vector 70 in an n-dimensional space 72, where n represents that number of sleep phenotyping parameters for which parameter module 38 has determined a score, and the individual scores are the coordinates of the vector. In this embodiment, an example of which is illustrated in FIG. 5, the n-dimensional space may be divided into regions A, B, C, and D. The regions may be predetermined to correspond with clusters of sleep phenotypes that respond positively to the same types of treatment. Phenotyping module 40 then prescribes the course of treatment for the sleep related breathing disorder(s) suffered by subject 12 that corresponds to the region in which the vector associated with subject 12 resides. In the example shown in FIG. 5, space 72 includes phenotype clusters and potential therapies for the following parameters, Perit, Loop Gain, and Arousal Threshold. Each potential therapy is indicated with a shaded ellipse. In this example, the patient exhibits a phenotype based on Pcrit, Loop Gain, and Arousal Threshold measurements, suggesting that a neuro pharmaceutical treatment would be optical for him/her. It can thus be appreciated that the type of therapy believed to be optimal for a given patient will depend on the phenotyping FIG. 4 illustrates a method 44 of determining a sleep phenotyping parameter of a subject. It should be appreciated that although various operations of method 44 are disclosed hereafter as being performed and/or executed by components of system 10 (illustrated in FIG. 1 and described above), this is for illustrative purposes only. In other embodiments, method 44 can be implemented by a variety of systems and in a variety of contexts.

Method 44 includes an operation 46, at which one or more output signals are generated that convey information related to one or more physiological functions of the subject. The one or more physiological functions indicate a sleep stage of the subject. In one embodiment, operation 46 is performed by a sleep sensor similar to sleep sensor 14 (illustrated in FIG. 1 and described above).

At an operation 48, a current sleep stage of the subject is determined based on the output signals generated at operation 46. In one embodiment, operation 48 is performed by a sleep module within a processor similar to sleep module 30 within processor 20 (illustrated in FIG. 1 and described above).

At an operation 50, a determination is made as to whether a trigger condition has been satisfied. Satisfaction of the trigger condition indicates that the stability of the subject's sleep is suitable for testing to determine information related to the sleep phenotyping parameter. The determination at operation 50 may be based on one or both of the output signals generated at operation 46 and the current sleep stage of the subject determined at operation 48. In one embodiment, operation 50 is performed by a trigger module within a processor similar to trigger module 32 within processor 20 (illustrated in FIG. 1 and described above).

If the trigger condition is determined at operation 46 not to be satisfied, then method 44 returns back to operation 46 and does not continue in determining the sleep phenotyping parameter. If the trigger condition is determined at operation 50 to be satisfied, then method 44 proceeds to an operation 52. It should be appreciated from the discussion of the functionality of trigger module 32 above, that in one embodiment, operation 50 is not a "one-time" determination, but instead includes a continuous or frequent monitoring of the sleep of the subject to ensure that the trigger condition continues to be satisfied throughout method 44 as information that enables the determination of the sleep phenotyping parameter is gathered.

At operation 52 one or more output signals are generated that convey information related to one or more physiological functions related to the sleep phenotyping parameter. In one embodiment, operation 52 is performed by a parameter sensor similar to parameter sensor 16 (illustrated in FIG. 1 and described above). It should be appreciated that in one embodiment, the one or more output signals are generated without regard for the determination made at operation 50, but the output signal(s) generated at operation 52 are not implemented in the determination of the sleep phenotyping parameter unless the trigger condition is determined to have been satisfied at operation 50.

At an operation 54 a stimulus is provided to the subject. The stimulus is provided to the subject such that the response of the subject to the stimulus enables the sleep phenotyping parameter to be determined from the output signals generated at operation 52. In one embodiment, operation 54 is performed by a stimulus generator similar to stimulus generator 18 (illustrated in FIG. 1 and described above). The stimulus generator may be controlled by a stimulus module within a processor similar to stimulus module 34 within processor 20 (illustrated in FIG. 1 and described above). It should be appreciated from the discussion above regarding the particulars of determining specific sleep phenotyping parameters that operation 54 is not included in method 44 for every phenotyping parameter, but only for those parameters for which provision of a stimulus facilitates determination.

At an operation 56 a determination is made as to whether a predetermined event has occurred. For example, in one embodiment, the predetermined event includes a respiratory event (e.g., flow limited breathing, an airway obstruction (complete or partial), snoring, etc.). The determination made at operation 56 is made based on the output signals generated at one or both of operations 46 and 52. In one embodiment, operation 56 is performed by an event module within a processor similar to event module 36 within processor 20. It should be appreciated from the foregoing discussion related to the determination of specific sleep phenotyping parameters that operation 56 is not included in method 44 for every phenotyping parameter, but only for those parameters for which the subjects response to the event facilitates determination.

At an operation 58 information related to the sleep phenotyping parameter is determined. In one embodiment, operation 58 is performed by a parameter module within a processor similar to parameter module 38 within processor 20 (illustrated in FIG. 1 and described above).

At an operation 60 the information related to the sleep phenotyping parameter determined at operation 58 is stored.

In one embodiment, the information is stored within a storage module similar to storage module 22 (illustrated in FIG. 1 and described above).

At an operation 62, a sleep phenotype of the subject is determined based on the information determined at operation 58. In one embodiment, operation 62 is performed by a phenotype module within a processor similar to phenotype module 40 within processor 20 (illustrated in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it should be understood that the present invention contemplates that, to the extent possible, one or more features of any embodiment can be combined with one or more features of any other embodiment.

What is claimed is:

1. A system configured to determine two or more sleep phenotyping parameters of a sleeping subject, the system comprising:

a sleep sensor configured to generate one or more output signals that convey information related to one or more physiological functions that indicate a sleep stage of a subject that is asleep, the sleep stage of the sleeping subject indicative of the depth of sleep of the sleeping subject;

a stimulus generator configured to selectively provide a stimulus to the sleeping subject, wherein a response of the sleeping subject to the stimulus enables information related to phenotyping parameter is a metric that quantifies aspects of physiology and/or physiological performance of the subject that characterizes a sleep phenotype of the subject, wherein the two or more sleep phenotyping parameters consist of two or more of a critical pharyngeal closing pressure, upper airway vibration characteristics, upper airway muscle responsiveness, arousal threshold, or ventilatory control feedback loop-gain;

a parameter sensor configured to generate one or more output signals that convey information related to one or more physiological functions related to the two or more sleep phenotyping parameters of the sleeping subject; and a processor configured to receive the one or more output signals generated by the parameter sensor, the processor being in operative communication with the stimulus generator, the processor being configured (i) to determine a current sleep stage of the sleeping subject based on the one or more output signals generated by the sleep sensor, (ii) to determine, based on the one or more output signals received from the sleep sensor, whether a trigger condition related to the current sleep stage of the sleeping subject is satisfied, and (iii) to control the stimulus generator to provide the stimulus to the sleeping subject if the trigger condition is satisfied, wherein the trigger condition comprises a requisite sleep stage such that provision of the stimulus to the sleeping subject is triggered responsive to determination by the processor that the current sleep stage has reached the requisite sleep stage;

wherein the processor is further configured to determine the information related to the two or more sleep phenotyping parameters based on the one or more output signals generated by the parameter sensor subsequent to the stimulus generator providing the stimulus to the sleeping subject, wherein the processor is configured such that the information related to the two or more sleep phenotyping parameters comprises two or more metric scores that represent the two or more sleep phenotyping parameters; and wherein the two or more metric scores are coordinates of a vector in an n-dimensional vector space with regions that correspond to sleep phenotypes that respond positively to the same types of treatment.

2. The system of claim 1, wherein the trigger condition comprises a threshold measurement of at least one of the one or more physiological functions determined from the one or more output signals generated by the sleep sensor.

3. The system of claim 2, wherein the trigger condition further comprises a predetermined amount of time for which the at least one of the one or more physiological functions must breach the threshold before the trigger condition is satisfied.

4. The system of claim 1, wherein the processor is further configured to control the stimulus generator to cease or pause the provision of the stimulus to the sleeping subject if the trigger condition is no longer satisfied.

5. The system of claim 1, further comprising a storage module, and wherein the processor is further configured to store information, to the storage module, related to the one or more output signals generated by the parameter sensor if the stimulus generator provides the stimulus to the sleeping subject.

6. The system of claim 5, wherein the processor is further configured to store information, to the storage module, regarding the provision of the stimulus to the sleeping subject.

7. The system of claim 1, wherein the processor is further configured to determine a current sleep stage of the subject based on the one or more output signals generated by the sleep sensor, and wherein the trigger condition further comprises a predetermined amount of time such that provision of the stimulus to the sleeping subject is triggered if the current sleep stage determined by the processor has been the requisite sleep stage for at least the predetermined amount of time.

8. The system of claim 1, wherein the response of the subject to the stimulus comprises one or more of a breathing obstruction, a flow limited breath, an arousal, snoring, or an airway collapse.

9. The system of claim 1, wherein the two or more sleep phenotyping parameters consist of the critical pharyngeal closing pressure and one or more of upper airway vibration, upper airway muscle responsiveness, arousal threshold, or loop gain; wherein the critical pharyngeal closing pressure is determined by the processor based on a stimulus pressure delivered to the subject and a respiration flow rate of the subject; and wherein the critical pharyngeal closing pressure corresponds to the stimulus pressure delivered to the subject that causes the respiration flow rate to go to zero.

* * * * *